United States Patent
Thomke et al.

(10) Patent No.: US 8,523,923 B2
(45) Date of Patent: Sep. 3, 2013

(54) CLAMPING AND ARTICULATION ELEMENT

(75) Inventors: Roland Thomke, Bellach (CH);
Christian Lutz, Mönkeberg (DE);
Vinzenz Burgherr, Bern (CH); Damian Fankhauser, Bern (CH)

(73) Assignee: Stryker Trauma SA (CH)

(*) Notice: Subject to any disclaimer, the term of this patent is extended or adjusted under 35 U.S.C. 154(b) by 1379 days.

(21) Appl. No.: 11/641,600

(22) Filed: Dec. 19, 2006

(65) Prior Publication Data
US 2007/0198012 A1    Aug. 23, 2007

(30) Foreign Application Priority Data

Feb. 21, 2006    (EP) .................................... 06110244

(51) Int. Cl.
*A61B 17/60*    (2006.01)

(52) U.S. Cl.
USPC ............... 606/324; 606/54; 24/335; 24/459; 403/385

(58) Field of Classification Search
USPC .............. 606/277, 324, 54–59; 403/385, 403/344, 316, 373; 24/335, 135 R, 459, 24/525, 569
See application file for complete search history.

(56) References Cited

U.S. PATENT DOCUMENTS

| | | | |
|---|---|---|---|
| 4,483,334 A | 11/1984 | Murray | |
| 4,620,533 A | 11/1986 | Mears | |
| 4,648,388 A | 3/1987 | Steffee | |
| 4,890,631 A * | 1/1990 | Hardy | 606/59 |
| 5,047,029 A * | 9/1991 | Aebi et al. | 606/264 |
| 5,285,556 A | 2/1994 | Shorin et al. | |
| 5,290,288 A | 3/1994 | Vignaud et al. | |
| 5,380,325 A | 1/1995 | Lahille et al. | |
| 5,741,252 A | 4/1998 | Mazzio et al. | |
| 5,752,954 A | 5/1998 | Mata et al. | |
| 5,810,817 A | 9/1998 | Roussouly et al. | |
| 5,938,663 A | 8/1999 | Petreto et al. | |
| 5,947,965 A | 9/1999 | Bryan | |
| 6,022,348 A * | 2/2000 | Spitzer | 606/54 |
| 6,080,153 A | 6/2000 | Mata et al. | |
| 6,146,383 A | 11/2000 | Studer et al. | |
| 6,267,765 B1 | 7/2001 | Taylor et al. | |

(Continued)

FOREIGN PATENT DOCUMENTS

| | | |
|---|---|---|
| DE | 19854347 | 6/1999 |
| EP | 1 184 000 | 3/2002 |
| EP | 1627608 | 2/2006 |

OTHER PUBLICATIONS

Search Report from EP 1 627 608 A1 dated Jan. 27, 2005.

*Primary Examiner* — Eduardo C Robert
*Assistant Examiner* — Julianna N Harvey
(74) *Attorney, Agent, or Firm* — Lerner, David, Littenberg, Krumholz & Mentlik, LLP

(57) ABSTRACT

A two-piece clamping element comprises two separate, i.e., non-integral, opposing first and second clamping jaws forming a laterally open cavity to receive a pin or rod-shaped element. Each clamping jaw has a bore aligned with one another to receive a screw, wherein a pivot bearing is arranged opposite said cavity allowing the two opposing clamping jaws to come in contact to one another. The pivot bearing comprises at least one set of complementary part-cylindrical bearing surface portions. An anti-rotation pin extends between the two jaw members.

16 Claims, 5 Drawing Sheets

(56) References Cited

U.S. PATENT DOCUMENTS

| | | |
|---|---|---|
| 6,277,069 B1 | 8/2001 | Gray |
| 6,342,054 B1 * | 1/2002 | Mata ............................ 606/59 |
| 6,616,664 B2 | 9/2003 | Walulik et al. |
| 6,652,523 B1 | 11/2003 | Evrard et al. |
| 6,702,814 B2 | 3/2004 | Walulik et al. |
| 6,749,361 B2 | 6/2004 | Hermann et al. |
| 6,842,949 B2 | 1/2005 | Warren |
| 6,872,209 B2 | 3/2005 | Morrison |
| 6,916,319 B2 | 7/2005 | Munting et al. |
| 7,131,972 B2 * | 11/2006 | Mazda et al. ............... 606/250 |
| 2002/0026190 A1 * | 2/2002 | Walulik et al. ............... 606/57 |
| 2002/0077629 A1 * | 6/2002 | Hoffman et al. ............. 606/59 |
| 2004/0010253 A1 | 1/2004 | Morrison |
| 2006/0039750 A1 | 2/2006 | Thomke et al. |

* cited by examiner

CLAMPING AND ARTICULATION ELEMENT

CROSS-REFERENCE TO RELATED APPLICATIONS

The present application claims priority from European Patent Application No. EP 06 110 244.8 filed on Feb. 21, 2006, the disclosure of which is hereby incorporated by reference herein.

BACKGROUND OF THE INVENTION

The invention pertains to a clamping element for the clamping of a rod-shaped element of an articulation element, particularly a clamping element, of an articulation element for the stabilization of bone fractures. The invention also pertains to an articulation element with two clamping elements and with one at least two-piece locking device, and optionally an anti-rotation device.

U.S. Patent Publication 2003/0181911 describes a single-piece clamping element with two opposing cavities and one laterally open cavity to receive a clamping jaw forming a rod-shaped element and a hinge, which is arranged opposite the cavity, connecting the clamping jaws so that they are movable on top of each other, with each clamping jaw having one bore each aligned flush with one another.

This clamping element has the advantage that an articulation can be produced with two identical clamping elements arranged next to one another, inserting a connecting screw through the bore, which is screwed into an internally threaded nut to close the clamping jaws.

From U.S. Pat. No. 5,752,954 an articulation is known consisting of two times two individual clamping jaw elements and one central screw. This articulation allows the lateral insertion of one or two rod-shaped elements into the corresponding cavities. U.S. Pat. No. 5,752,954 has a spring, which spring tension allows the clipping in of the rod-shaped elements and holding the jaw elements on the rod-shaped elements before the articulation element is blocked. U.S. Pat. No. 6,616,664 provides for narrow lateral lever arms to hold laterally inserted rod-shaped elements before the articulation is blocked. U.S. Pat. No. 6,342,054 has an external spring.

SUMMARY OF THE INVENTION

Based on this state of technology, it is one role of the invention at hand to provide a two-piece clamping element which allows the lateral insertion of a rod-shaped element and which, when utilized dually, is directly applicable as an articulation element. It is another object of the invention to obtain a two-piece clamping element with advantages of a single-piece clamping element, e.g. the working connection of the two clamping jaws.

Another goal of the invention is the creation of a cost-effective disposable clamping element, particularly made of a synthetic material (such as plastic) injection molding, which does not have the structural disadvantages of X-ray transparent clamping elements as in U.S. Publication 2003/0181911. Especially it is an object of the invention to realize a disposable clamping element being able to support and transmit large pressure forces.

Based on the known state of technology, another role of the invention is also to provide an improved articulation element. Such an improved articulation element is shown in U.S. Patent Publication 2006/0039750 assigned to the assignee of the present invention.

A two-piece clamping element is provided comprising two separate non-integral opposing first and second clamping jaws forming a laterally open cavity to receive a rod-shaped element, with each clamping jaw having a bore aligned with one another.

A pivot bearing is arranged opposite the cavity bringing the two opposing clamping jaws in contact to one another and thereby making them movable towards and away from one another. Each clamping jaw has a bore, aligned with one another. The bores are arranged between the cavity and the pivot bearing.

A first clamping jaw has an anti-rotation device on its exterior or a receptacle for receiving an anti-rotation device.

An articulation element can be formed from two clamping elements in which the clamping elements are arranged on top of one another with their first clamping jaws adjacent one another. The articulation element has one at least two-piece locking shaft with a first part of the locking shaft insertable through a bore of the second clamping jaw of one clamping element, and with a second part of the locking shaft insertable through a bore of the first clamping jaw of the other clamping element. One or the other or both parts of the locking shaft being able to be brought in contact with one another through the bores in the first clamping jaws. The first and second clamping jaws of the clamping elements can be blocked with the locking device. The articulation element has an anti-rotation device is arranged between the first clamping jaws that are arranged on top of one another, the anti-rotation device having a central bore. The anti-rotation device is preferably a plate whose material is preferably harder than the material of the clamping elements and which has ridges formed on both sides of the plate. The anti-rotation device can also be a cylinder whose material in a floor and a lid area thereof is preferably harder than the material of the clamping elements, and which preferably consists of a flexible, compressible material in the solid material part, in particular synthetic foam. The locking device includes a cylindrical screw and a conical nut, the conical nut preferably has a stop shoulder for a self-locking screw, which can be inserted in an internal thread in the cylindrical screw. A hollow spring enveloping the locking device is used as an anti-rotation device or as an additional anti-rotation device.

By equipping the two-piece clamping elements with functionally different first and second clamping jaws, two clamping elements can be placed on top of one another each with their first clamping jaws, to form an articulation element in a simple manner.

BRIEF DESCRIPTION OF THE DRAWINGS

Now the invention is more closely described with reference to the drawings and with the aid of a number of embodiments.

DETAILED DESCRIPTION

Figure 1:
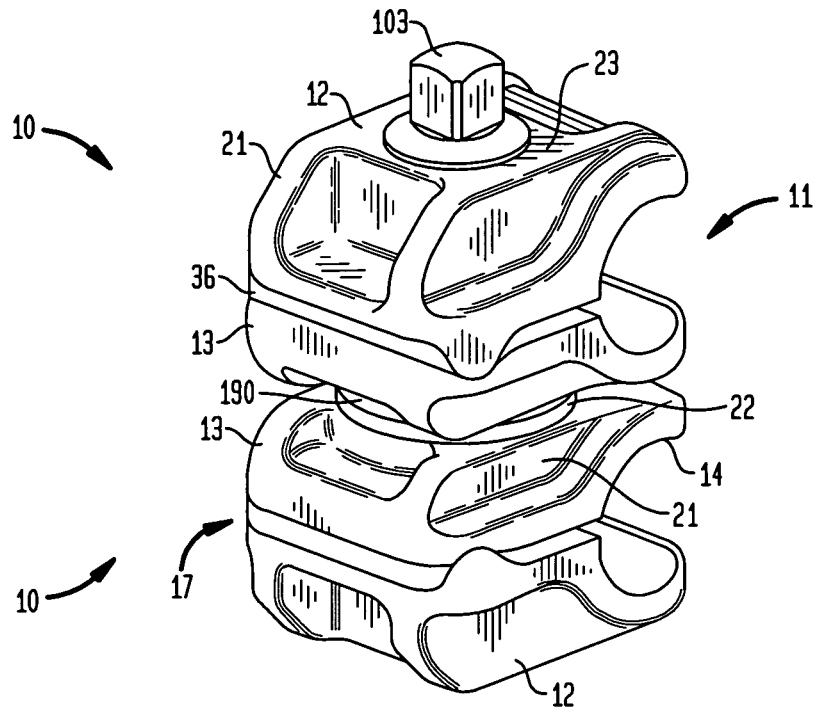
FIG. 1 shows a perspective view of an articulation element with two clamping elements per a first embodiment of the invention.
Figure 2:
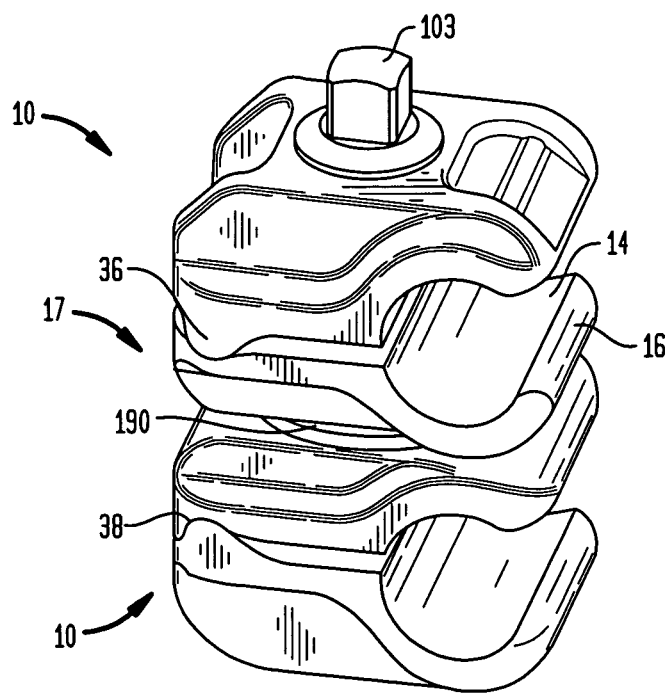
FIG. 2 shows a different perspective view of the articulation element of FIG. 1.
Figure 3:
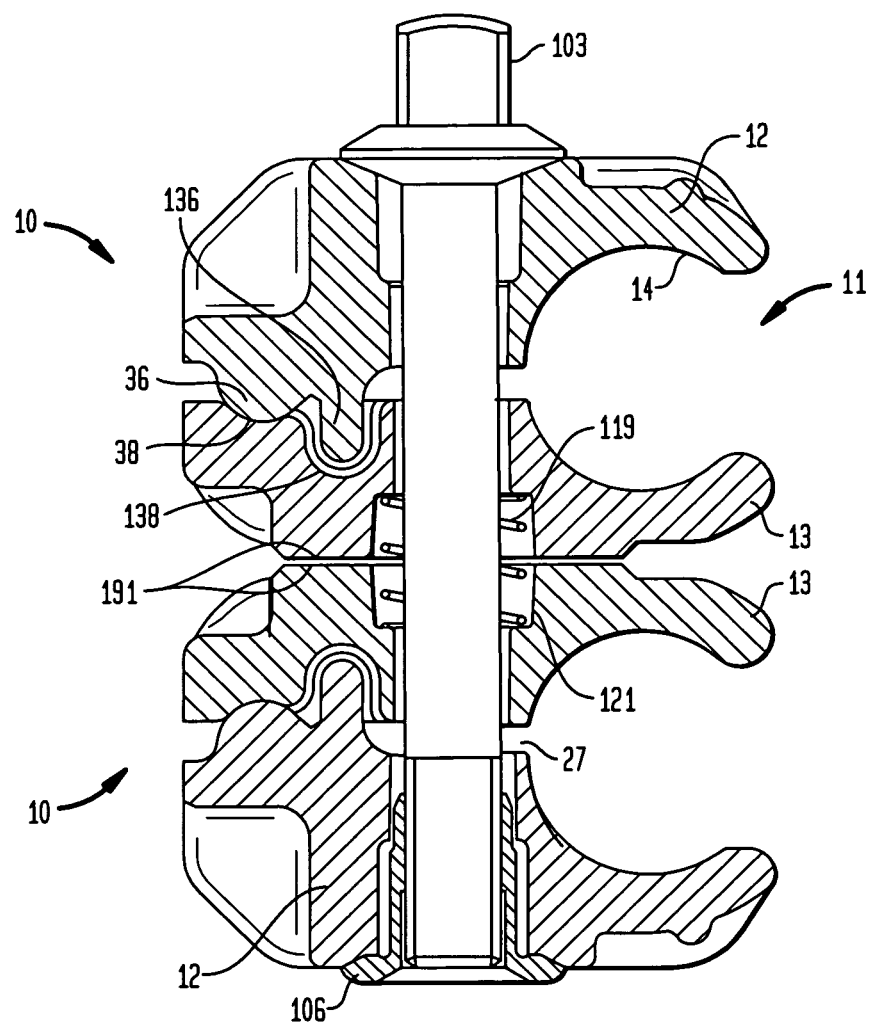
FIG. 3 shows a cross-section view of the articulation element of FIG. 1 or 2.

FIGS. 1 to 3 show a first embodiment of an articulation element with two clamping elements 10 per the invention. FIGS. 1 and 2 show two perspective views at different angles from the top. The two-part clamping element 10 has two clamping jaws 12 and 13 creating together one cavity 11 to receive a rod-shaped element. The cavity 11 is formed by transversely running grooves 14. The outer edges 16 of the side facing clamping jaws 12 and 13 are slanted to simplify the lateral insertion of a rod-shaped element. Across from the cavity 11 and the slanted outer edges 16, a pivotal bearing 17 is arranged, comprising complementary pivotal surfaces comprising semi-cylindrical portions 36 and complementary grooves 38 contacting clamping jaws 12 and 13.

When the clamping element 10 is intended for a rod with 4 to 6 millimeters in diameter, the opening at the free ends has a diameter of, for instance, 2 millimeters in a resting position. If the clamping element 10 is intended for a rod with a diameter of 12 millimeters, the opening at the free ends has a diameter of, for instance, 9 millimeters in a resting position.

In the upper area of the clamping jaw 12 the area between cross ribs 21 has been excluded with the exception of a round screw receptacle 23. Screw receptacle 23, for instance, has a conical shoulder area or a step shoulder, whose purpose will be described later, which merges into a continuous bore in the top clamping jaw 12, which can be seen in FIG. 3.

In the lower clamping jaw 13 cross ribs 21 end in a ring flange 22, which, for instance, may have a flat recessed ring shaped step, where a weight and material saving recess advantageous for injection molding can be connected, with a bore in the center.

This continuous bore is aligned flush with the abovementioned bore in top clamping jaw 12. At the clamping element 10, it runs vertically to the axis of the cavity 11. The bore is cylindrical and in its interior, it may have guide ribs arranged in regular intervals. Of course, the number of guide ribs may be chosen freely, preferably between three or five ribs.

One clamping element 10 with the jaw parts 12 and 13 comprises a semi-cylindrical portions 36 running over the whole width of the jaw 12 and being directed to a complementary groove 38 in jaw 13. The stops 36 and 38 may be chosen shorter or in smaller portions with intermediate regions; however, the shown embodiment providing for a long pivotal bearing 17 is preferred. The stops 36 and 38 are running parallel to the cavity 11. Between the stops 36 and 38 and the vertically oriented bores for the screw is provided a pin 136 and a corresponding reception bore 138. The pin 136 can be seen in the cross-sectional view of FIG. 3, entering with play into the reception bore 138, to ensure that the jaws 12 and 13 are not rotating one against the other and to allow an easy introduction of a larger rod into the cavity 11 whereas the complementary stop surfaces 36 and 38 can loose contact but are guided by elements 136 and 138. The pin 136 can be symmetrical in view of his main axis but is preferably oblong in the transverse direction, e.g. parallel to surfaces 36 and groove 14.

Figure 4:
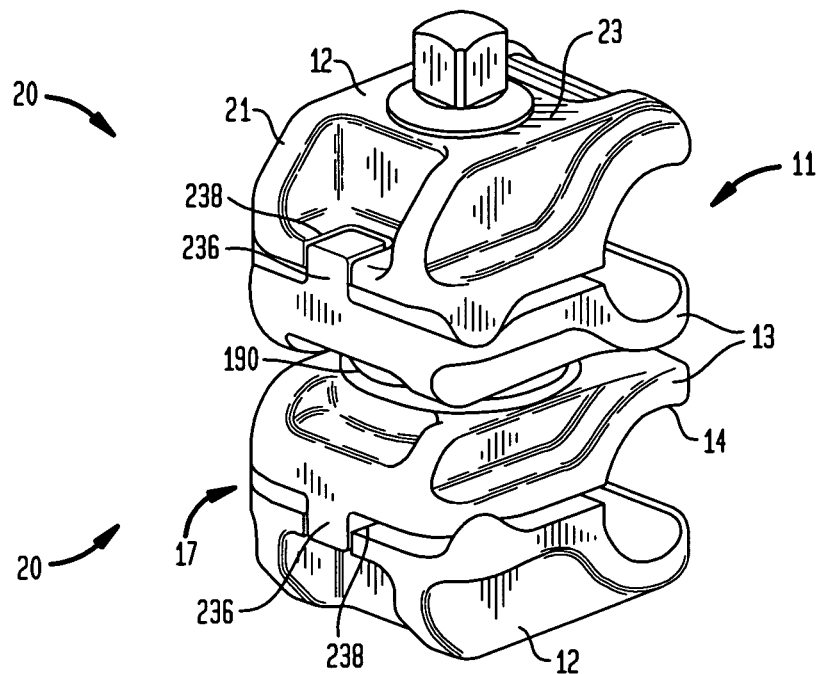
FIG. 4 shows a perspective view of an articulation element with two clamping elements per a second embodiment of the invention.
Figure 5:
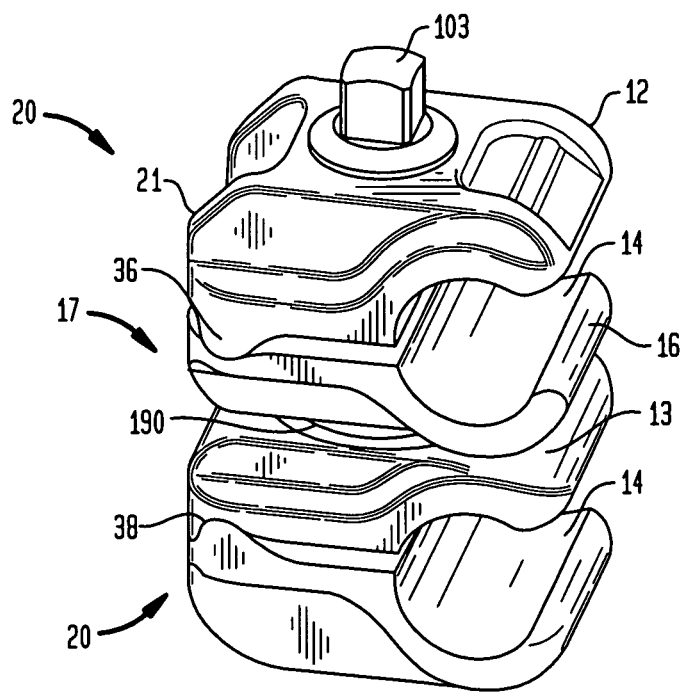
FIG. 5 shows a different perspective view of the articulation element of FIG. 4.
Figure 6:
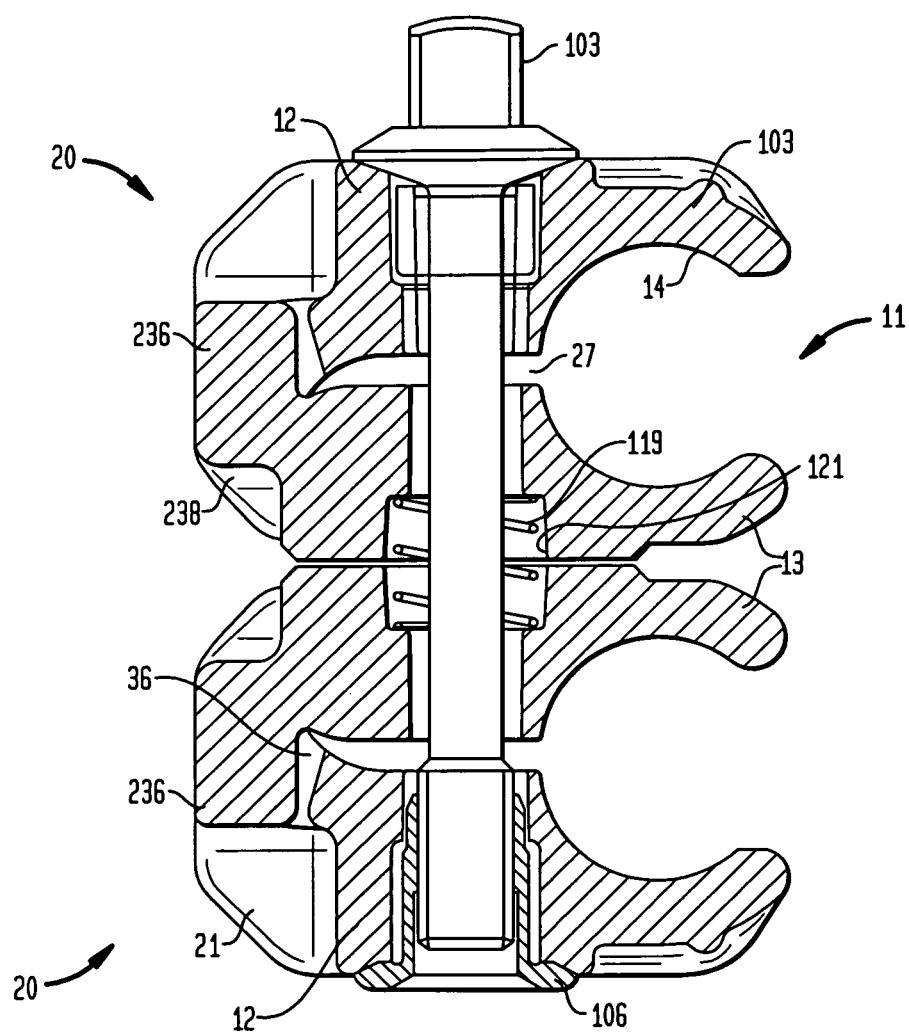
FIG. 6 shows a cross-section view of the articulation element of FIG. 4 or 5.

FIGS. 4 to 6 show a second embodiment of an articulation element with two clamping elements 20 per the invention.

FIGS. 4 and 5 show two perspective views at different angles from the top. The two-part clamping element 20 has two clamping jaws 12 and 13 creating together one cavity 11 to receive a rod-shaped element. All identical or similar features have received the same reference numerals as cavity 11 and grooves 14. Across from the cavity 11, a pivotal bearing 17 is arranged, comprising complementary pivotal surfaces comprising semi-cylindrical portions 36 and complementary grooves 38 contacting clamping jaws 12 and 13.

One clamping element 20 with the jaw parts 12 and 13 comprises two semi-cylindrical portions 36 running on the left and on the right side of a passage 238 of the jaw 12 and being directed to two complementary groove portions 38 on both sides of a blocking pin 236 in jaw 13. The stops surfaces 36 and 38 may also be chosen shorter; however, the shown embodiment providing for two rather long pivotal bearing surfaces 17 is preferred. The blocking pin 236 and the corresponding reception bore 238 are provided on the outer open side of the jaws 12 and 13. The pin 236 is—seen from above—rectangular to ensure that the jaws 12 and 13 of the clamping element 20 can not rotate one against the other.

In the first embodiment of FIG. 1 to 3 the pin 136 is provided in the jaw 12 whereas in the second embodiment of FIG. 4 to 6 the blocking pin 236 is provided in the jaw 13. This clearly shows that the features of the two embodiments can be mixed, the blocking pin 236 of FIG. 4 can be used within jaw 12 and the pin 136 of FIG. 1 can be used within jaw 13 with the complementary bores in the other jaws 13 and 12, respectively. However, the represented embodiments are preferred.

A spiral or coil spring 119 is arranged between surfaces 191 of the two clamping elements 10 or 20, which is supported by the spring receptacle 121. The spring receptacle 121 can form a hemispherical area; it can also be level and smooth; in particular, it can be rough to ensure a greater resistance of the spring 119 against twisting. The spring 119 pushes the two clamping elements 10 or 20 away from one another and is intended to secure the twisting of the two clamping elements 10 or 20 against one another. It does not secure the forcing apart of the jaws 12 and 13; they open against the forces acting upon the clipping in of the rods 101 and 102 in a radial direction with respect to grooves 14. The spring 119 can also be a disk spring package or another resilient element.

Figure 7:
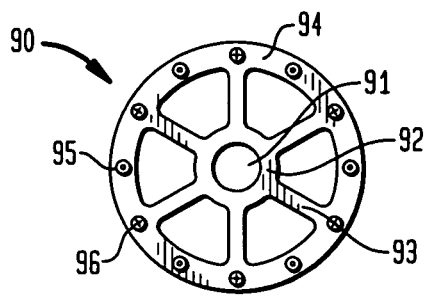
FIG. 7 shows a top view of an anti-rotation device for an articulation element per FIG. 1 or 4.

FIG. 7 shows a top view of an anti-rotation device 90 for an articulation element per FIG. 1. Anti-rotation device 90, for instance, is a thin metal plate with a central bore 91, a hub 92 and spokes 93. The outer rim 94, for instance, has successive punctured ridges 95 and recesses 96. For instance, they are arranged so that recesses 96 are always arranged opposite the six spokes 93 in this case, with each of the ridges 95 located intermittently.

It is clear that, a simple punching process to manufacture the plates of the anti-rotation device 90 is used, that ridges 95 seen from above are recesses seen from below. Punctured ridges 95 and recesses 96 can be round, pyramidal or polygon shaped. They can run radially side by side in several rows, in a larger number than in FIG. 7 etc. In another alternate design, radial ribs can be used as well.

The anti-rotation device 90 is to be positioned between the two clamping elements 10, 20 at the position 190 as indicated in FIGS. 1, 2, 4 and 5. FIGS. 3 and 6 show that an anti-rotation device can also be achieved through the design of the material of the first clamping jaw 13, comprising rough elements to avoid rotation between the contacting jaws 13.

Figure 8:
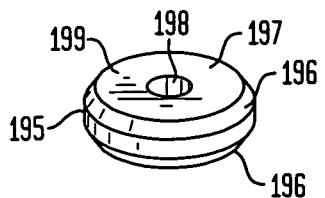
FIG. 8 shows a perspective view of another anti-rotation device for an articulation element.

The anti-rotation device can also be a flexible synthetic foam element 199 as per FIG. 8. Only upon the tightening of screw 103 the anti-rotation device 199 interlock and determine the angle position of the articulation element.

This is a flexible cylindrical element 199 with a central bore 198 for receiving screw 103. It can be used in the place of an anti-rotation device 90. The advantage is that its material on the bottom and lid surfaces 197 is harder and, in particular, can also be structured or span hard inserts to engage in a ring-shaped step. The clamping element 10 is then designed similar to the embodiment per FIG. 1, only the depth and the sidewalls are intended to receive the anti-rotation device 199. In the cylinder area, the element 199 is flexible to be compressed when screw 103 is tightened. The anti-twisting device is beveled and has conical slants 196 between the surface 195 and the lid or the floor area 197.

It is advantageous that the material in the floor and lid area of the anti-rotation device 199 is harder than the material of the clamping elements utilized, and in the solid material preferably consists of a flexible, compressible material, particularly synthetic foam.

The diameter of the anti-rotation device 90 or 199 is 30 millimeters and the contact surface (radial width) for the outer rim 94 is 3 millimeters. Instead of placing the ridges on element 90, the structures (ridges) can also be integrated in the material of the clamping jaw 13, for instance radial grooves.

Figure 9:
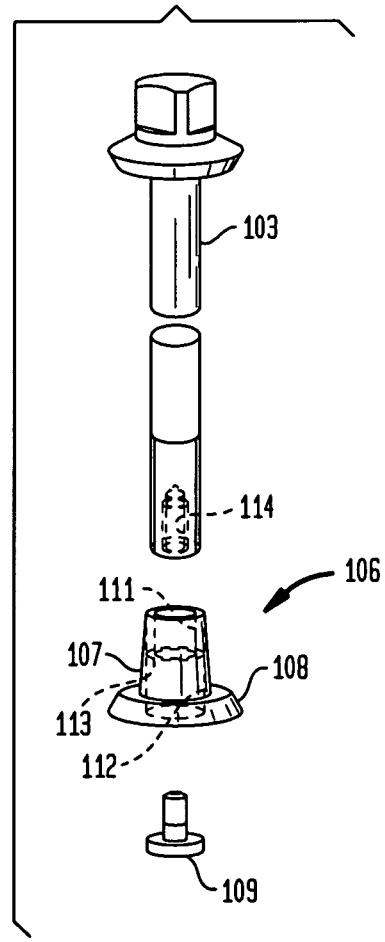
FIG. 9 shows a partially sectioned lateral view of a part of a locking screw, a nut and a self-locking bolt for an articulation element per one of the FIG. 1 to 6.

FIG. 9 shows a screw 103 which is to be inserted through the aligned bores, which can sit on the conical screw receptacle 23 with its conical flange 104. For tightening, screw 103 for instance has a square drive head 105. It is clear that instead of a square, a hexagon or a slit etc. can be utilized. Preferably, the shoulder 104 is designed to be complementary to the receptacle 23. A nut 106 is attached from the other side. The nut 106 has a slightly conical sleeve 107 and a conical flange 108 as a covering cap. The shape of flange 108 corresponds to the shape of screw receptacle 23 of clamping element 10 or 20. The sleeve 107 is inserted into one bore and, to the best advantage, protrudes into the other bore and/or through it. The sleeve 107 is fitted in the press fit; additionally, it can also have an external thread. It can be designed as a fit for one of the internal threads used in bore. Sleeve 107 has an internal thread 111 ending at 113 and has a surface 112 which engages jaw member 12.

In another design version, not illustrated in the drawings, a clamping element is equipped with a tilting, but torsion rigid, bearing for the nut. The clamping jaw 12 again has the conically opening bore. This bore, however, has a recess on the side facing away from the cavity 11, which can be a rectangular slit in particular. During the assembly, the cylindrical nut is inserted in the recess. A tolerance exists through the cylindrical nut, so that when a rod 102 is clipped into cavity 11 the top part 12 of the clamping element can be tilted as well. In order to ensure the fixation of screw 103 and to design the nut torsionally rigid, it has an appendage or projection, which protrudes into the said recess with lateral tolerance. In a lateral view of the clamping element, the projection has a tolerance in the recess to permit the tilting motion of top part 12. In addition to the nut with projection, other design versions are possible, for instance, an L-shaped flattened nut, which, for example, has wobble rivets and is punched, so that an appendage protrudes into a corresponding nut in top part 12 and produces the torsion rigidity.

The nut 106 has an internal thread that fits the complementary external thread of screw 103. Through the tightening of screw 103 opposite nut 106, the two clamping elements 10 and 20 are pulled together. Then, by exerting pressure, a rod can be inserted laterally in the respective cavity. Since the diameters of the rods are larger than the opening at the free ends, it is protected from falling out. Through a roughening of grooves 14, not illustrated in the drawings, it is also protected from a simple longitudinal displacement.

If screw 103 is tightened further, clamping jaws 12 and 13 are moved closer towards one another against the resetting force of the hinge bearing 17 and are finally completely blocked in their angled position through the use of the plate of anti-rotation device 90 placed between the clamp elements. At the same time, this fully secures the rods in grooves 14 against longitudinal displacement as well as against twisting by minimizing the cavity 11. Self-locking screw 109 which extends into threaded bore 114 can be utilized here as well. Preferably the nut 106 is designed as a continuous sleeve.

When screw 103 is opened, nut 106 remains in the one clamping element. The anti-rotation device 90 has impressed itself into the softer material of jaw 13. Said impression makes it preferable—with the exception of an immediate tightening of the screw in this or another place of an external fixator clamping element used for the same patient—to use said clamping element only once and to throw it away after use. The material used for the clamp may be PEEK (Poly Esther Ether Ketone), and may have chopped carbon fiber reinforcement for extra strength. This allows the two pieces of the polymeric clamp to be injection molded. The pressed in traces of the anti-rotation device in the step is a sign of use for the clamping element, so that the user can see that the reuse of the product can be excluded.

In the resting position of the clamping elements 10 and 20, clamping jaws 12 and 13 urged together by the spring force and the distance of the slit 27 is reduced. When screw 103 is tightened, the slit is minimized. Through the central transfer of force via the screw and nut elements 104 and 108 on the identical areas, the slit 27 is minimized in its thickness until the groove 14 contacts the rod in the cavity 11. Then the (upper) clamping jaw 12 with the ribs 21 deviates around the rod and the semi-cylindrical region 36 touches down on the complementary area 38. When screw 103 is tightened further, the blocking effect sets in as of this time and the unit semi-cylindrical region 36—complementary area 38 takes over the bearing function.

Instead of a screw 103, another locking device can be used, for instance a clamping lever or a bayonet catch.

It is emphasized that the term embodiment in the previously mentioned description does not mean that only the elements described with respect to the respective clamping element or articulation element are subject of the invention. In particular, these are also combinations of the characteristics described in objects of various embodiments and FIGS. For instance, a clamping element is an object of the invention, which has the bore and nut per FIG. 3, a counter nut 109 per FIG. 9 and non-skid elements 99 for the rods per FIG. 8 or a part thereof. A corresponding articulation element can be comprised of any two random above-mentioned clamping elements, if they can be utilized for the selected anti-rotation device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A two-piece clamping element comprising two separate opposing first and second clamping jaws each having a recessed surface extending along a first axis forming a laterally open expandable cavity extending between first and second outer surfaces of each clamping jaw to receive a rod-shaped element, with each clamping jaw having a bore aligned with one another, wherein a pivot bearing is arranged opposite said cavity allowing the two opposing clamping jaws to come into contact with one another, wherein the pivot bearing comprises at least one set of complementary pivot bearing surfaces portions wherein the set of complementary pivot bearing surfaces portions are pivotally engaged and comprise a protrusion with a part-cylindrical convex surface in the first clamping jaw and a complementary groove with a part-cylindrical concave surface in the second clamping jaw, the part-cylindrical surfaces of the protrusion and complementary groove of the pivot bearing each extend across the entire distance between the first and second outer surfaces of the clamping jaws along an axis parallel to the first axis, the convex and concave part-cylindrical surfaces are in contact and pivot against one another as the laterally open cavity expands.

2. The clamping element as set forth in claim 1, wherein a first clamping jaw has an anti-rotation device on its exterior or a receptacle for receiving an anti-rotation device.

3. The clamping element as set forth in claim 1 wherein the part-cylindrical protrusion and groove extend over a width of the clamping jaw in a direction parallel to the laterally extending cavity.

4. The clamping element as set forth in claim 1, wherein a rotation avoiding pin is provided in one of the jaws whereas a corresponding similar reception bore for the rotation avoiding pin is arranged in the other of the jaws.

5. The clamping element as set forth in claim 4, wherein the rotation avoiding pin is provided between the complementary pivot bearing surfaces portions and cavity.

6. The clamping element as set forth in claim 4, wherein the rotation avoiding pin is arranged such to divide the complementary bearing surfaces portions in two side parts.

7. An articulation element having first and second two-piece clamping elements as set forth in claim 1, which clamping elements are arranged on top of one another with their first clamping jaws adjacent one another, and having an at least two-piece locking device with a first part of the locking device insertable through a bore of the second clamping jaw of the first clamping element, and with a second part of the locking device insertable through a bore of the first clamping jaw of the second clamping element, and with one or the other or both parts being able to be brought in contact with one another through the bores in the first clamping jaws, and where the first and second clamping jaws of the first and second clamping elements can be blocked with the locking device.

8. A two-piece clamping element for an external bone fixation system comprising:
a first piece having a bore therethrough and a rod or pin receiving recessed surface extending along a first axis between first and second side surfaces of the first piece, the first piece having an arcuate pivot bearing surface open to an external surface thereof and an anti-rotation element associated with the external surface;
a second piece having a bore therethrough alignable with the bore in the first piece and a rod or pin receiving recessed surface in an external surface of the second piece extending between first and second side surfaces along a second axis parallel to the first axis, the external surface of the second piece having an arcuate pivot bearing surface complementary to the first piece arcuate pivot bearing surface for sliding engagement therebetween and an anti-rotation element associated therewith adjacent the arcuate pivot bearing surface and engagable with an anti-rotation element of the first piece when the external surfaces of the first and second pieces are juxtaposed wherein the complementary arcuate pivot bearing surface on the first and second pieces comprise part-cylindrical protrusions with a convex contact surface and complementary part-cylindrical grooves with a concave contact surface, both the concave and convex contact surfaces extending across the entire distance between the first and second side surfaces of the first and second pieces along an axis parallel to the first and second axis which convex and concave part-cylindrical pivot contact surfaces on the first and second pieces contact and pivot against one another when a rod or pin is inserted laterally into the recessed surfaces of the juxtaposed first and second pieces.

9. The two-piece clamping element as set forth in claim 8, wherein the anti-rotation element on the first piece is an integrally formed pin element extending from the external surface thereof and the anti-rotation element on the second piece is a recess open to the external surface thereof for receiving the pin.

10. The two-piece clamping element as set forth in claim 9, wherein the anti-rotation pin and recess are centrally located between the first and second side surfaces of each of the first and second pieces.

11. The two-piece clamping element as set forth in claim 10 wherein the part-cylindrical protrusion and groove are located adjacent both of the first and second side surfaces of the first and second pieces.

12. The two-piece clamping element as set forth in claim 8 wherein the first and second pieces are made of a molded polymeric material.

13. The clamping element as set forth in claim 8 wherein the part-cylindrical protrusion and groove extend over a width of the clamping jaw in a direction parallel to the laterally extending cavity.

14. An articulation element for an external bone fixation system comprising two clamping elements as set forth in claim 8 having a locking pin extending through aligned bores of each clamping element and a spring element located around the pin between the two clamping elements.

15. The articulation element as set forth in claim 14 further comprising a means for preventing the relative rotation of the two clamping elements about the locking pin.

16. A two-piece clamping element comprising two separate opposing first and second clamping jaws forming an expandable laterally open cavity extending between outer surfaces of the first and second clamping jaws along a first axis to receive a rod-shaped element, with each clamping jaw having a bore aligned with one another, wherein a pivot bearing is arranged opposite said cavity allowing the two opposing clamping jaws to come in contact to one another, wherein the pivot bearing comprises at least one set of slidably engaged complementary bearing surfaces portions extending along a second axis parallel to the first axis of the laterally open cavity, wherein a rotation avoiding pin is provided in one of the jaws whereas a corresponding similar reception bore for receiving the rotation avoiding pin is arranged in the other of the jaws, the complementary bearing surfaces respectively having convex and concave surfaces being part-cylindrical in cross-section about the second axis and are in contact across the entire distance between the outer end surfaces of the first and second clamping jaws, the complimentary contacting convex and concave bearing surfaces pivot against one another about the second axis as the laterally open cavity expands upon reception of the rod-shaped element.

* * * * *